United States Patent
Zhang et al.

(10) Patent No.: US 12,385,094 B2
(45) Date of Patent: Aug. 12, 2025

(54) MOLECULAR MARKER DETECTION AND REGULATING METHODS IN DE-SERVITIZATION STATE OF CELLS

(71) Applicant: NANJING UNIVERSITY, Nanjing (CN)

(72) Inventors: Chenyu Zhang, Nanjing (CN); Zhen Zhou, Nanjing (CN); Xiuting Hu, Nanjing (CN); Jing Li, Nanjing (CN); Xinyan Zhou, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 969 days.

(21) Appl. No.: 17/604,707

(22) PCT Filed: Apr. 17, 2020

(86) PCT No.: PCT/CN2020/085364
§ 371 (c)(1),
(2) Date: Oct. 18, 2021

(87) PCT Pub. No.: WO2020/211841
PCT Pub. Date: Oct. 22, 2020

(65) Prior Publication Data
US 2022/0195525 A1  Jun. 23, 2022

(30) Foreign Application Priority Data
Apr. 18, 2019  (CN) .......................... 201910314706.8

(51) Int. Cl.
*C12Q 1/6883* (2018.01)
*A61K 31/7088* (2006.01)
*C12N 15/113* (2010.01)

(52) U.S. Cl.
CPC ........ *C12Q 1/6883* (2013.01); *A61K 31/7088* (2013.01); *C12N 15/113* (2013.01); *C12N 2320/30* (2013.01); *C12Q 2600/178* (2013.01)

(58) Field of Classification Search
None
See application file for complete search history.

(56) References Cited

FOREIGN PATENT DOCUMENTS

| | | |
|---|---|---|
| CN | 104894259 A | 9/2015 |
| JP | 2017029116 A | 2/2017 |
| WO | 2011036091 A1 | 3/2011 |
| WO | 2014110230 A2 | 7/2014 |
| WO | 2020211841 A1 | 10/2020 |

OTHER PUBLICATIONS

International Search Report and Written Opinion; PCT Application No. PCT/CN2020/085364; mailed Jul. 23, 2020.
English translation of International Search Report; PCT Application No. PCT/CN2020/085364; mailed Jul. 23, 2020.
Cuomo, D. et al., "Transcriptional Landscape of Mouse-Aged Ovaries Reveals a Unique Set of Non-coding RNAs Associated with Physiological and Environmental Ovarian Dysfunctions", Cell Death Discovery, vol. 4, Dec. 5, 2018; article No. 112.
English abstract of CN104894259; retrieved from www.espacenet.com on Oct. 15, 2021.
Zhang, Xiaochen et al., snoRNA; Structure and Function of snoRNAs; Chinese Bulletin of Life Sciences, vol. 20, No. 2, Apr. 30, 2018.
Cuomo, Danila et al.: "Transcriptional landscape of mouse-aged ovaries reveals a unique set of non-coding RNAs associated with physiological and environmental ovarian dysfunctions", Cell Death Discovery, vol. 4, No. 1, pp. 1-14, Dec. 1, 2018.
Stepanov, Grigory A. et al.: "Regulatory Role of Small Nucleolar RNAs in Human Diseases", Biomed Research International, vol. 15, pp. 1-11, Jan. 1, 2015.
Supplementary European Search Report, EP App. No. 20792239.4, pp. 1-8, mailed Jan. 9, 2023.

*Primary Examiner* — Sean McGarry
(74) *Attorney, Agent, or Firm* — NKL Law; Bin Lu; Allen Xue

(57) ABSTRACT

The present invention provides a use for a small nucleolar RNA (snoRNA) or a detection reagent thereof, for use in detection of a servitization state of cells; moreover, detection and regulating methods for the snoRNA are established.

6 Claims, 3 Drawing Sheets
Specification includes a Sequence Listing.

SEQUENCE LISTING

<160> NUMBER OF SEQ ID NOS: 9

<210> SEQ ID NO 1
<211> LENGTH: 87
<212> TYPE: DNA
<213> ORGANISM: Artificial Sequence
<220> FEATURE:
<223> OTHER INFORMATION: cDNA corresponding to snoRNA

<400> SEQUENCE: 1
tcgctgtgat gatggattcc aaaaccattc gtagtttcca ccagaaatgc tgtgttggct    60
agttccttcc ttggatgtct gagcgaa                                        87

<210> SEQ ID NO 2
<211> LENGTH: 87
<212> TYPE: DNA
<213> ORGANISM: Artificial Sequence
<220> FEATURE:
<223> OTHER INFORMATION: cDNA corresponding to snoRNA

<400> SEQUENCE: 2
tcgctgtgat gatggattcc aaaaccattc gtagtttcca ccagaagtac tgtgttggct    60
agttccttcc ttggatgtct gagcgaa                                        87

<210> SEQ ID NO 3
<211> LENGTH: 78
<212> TYPE: DNA
<213> ORGANISM: Artificial Sequence
<220> FEATURE:
<223> OTHER INFORMATION: cDNA corresponding to snoRNA

<400> SEQUENCE: 3
cgcggatgat gacacctggg tatgctgcac actcccgact gcgtcgtggg gaagccaacc    60
ttggagagct gagcgtgc                                                  78

<210> SEQ ID NO 4
<211> LENGTH: 145
<212> TYPE: DNA
<213> ORGANISM: Artificial Sequence
<220> FEATURE:
<223> OTHER INFORMATION: cDNA corresponding to snoRNA

<400> SEQUENCE: 4
cttcagtgat gacacgatga cgagtcagaa tggccacgtc ttgctcttgg tccctgtcag    60
tgccatgttc tgtggtgctg tacatggttc ccttggcaaa agtgtcctgc gcactgattg   120
atttagaggc atttgtctga gaagg                                         145

<210> SEQ ID NO 5
<211> LENGTH: 99
<212> TYPE: DNA
<213> ORGANISM: Artificial Sequence
<220> FEATURE:
<223> OTHER INFORMATION: cDNA corresponding to snoRNA

<400> SEQUENCE: 5
tgataaccat ccttgctccc cgtgcctact cgggctgtgg gcgacaccat ggctgccctg    60
ggctgggcca gttgggccat tgcctgggga ctgagggca                           99

<210> SEQ ID NO 6
<211> LENGTH: 77
<212> TYPE: DNA
<213> ORGANISM: Artificial Sequence
<220> FEATURE:
<223> OTHER INFORMATION: cDNA corresponding to snoRNA

<400> SEQUENCE: 6
atcctagtga tgacaagacg acattgtcaa ccaatccccc acagggaat gaggacatgt     60 cctgcaattc tgaatgg                                                   77

<210> SEQ ID NO 7
<211> LENGTH: 88

```
<212> TYPE: DNA
<213> ORGANISM: Artificial Sequence
<220> FEATURE:
<223> OTHER INFORMATION: cDNA corresponding to snoRNA

<400> SEQUENCE: 7
aaacccattg gtgaaaatga tgaattctgg ggcgctgatt catgtgactt gaaaaaacgc    60
catccatttc ctgactcacc gcagattc                                      88

<210> SEQ ID NO 8
<211> LENGTH: 66
<212> TYPE: DNA
<213> ORGANISM: Artificial Sequence
<220> FEATURE:
<223> OTHER INFORMATION: cDNA corresponding to snoRNA

<400> SEQUENCE: 8
cgtctgtgat gttctgctat tacctacatt gtttgagcct catgaaaacc ccactggctg    60
agacgc                                                              66

<210> SEQ ID NO 9
<211> LENGTH: 68
<212> TYPE: DNA
<213> ORGANISM: Artificial Sequence
<220> FEATURE:
<223> OTHER INFORMATION: cDNA corresponding to snoRNA

<400> SEQUENCE: 9
acaagtgatg agtgacaaag ggacttaata ctgaaccatg gggttgaaat gaaatatgct    60
gatgtgct                                                            68
```

MOLECULAR MARKER DETECTION AND REGULATING METHODS IN DE-SERVITIZATION STATE OF CELLS

CROSS REFERENCE TO RELATED APPLICATIONS

The present application is the U.S. National Phase under 35 U.S.C. § 371 of International Application No. PCT/CN2020/085364, filed Apr. 17, 2020, which claims the priority of the Chinese patent application filed with the Chinese Patent Office on Apr. 18, 2019, with the application number CN201910314706.8 and the invention title of "MOLECULAR MARKER DETECTION AND REGULATING METHODS IN DE-SERVITIZATION STATE OF CELLS", the entire contents of each of which are herein incorporated by reference.

SEQUENCE LISTING

A Sequence Listing submitted herewith as an ASCII text file via EFS-Web is hereby incorporated by reference in accordance with 35 U.S.C. § 1.52(e). The name of the ASCII text file for the Sequence Listing is "WO2020211841A1 SEQ.TXT", and the size of the ASCII text file is 3 KB.

TECHNICAL FIELD

The invention belongs to the field of biotechnology, in particular to separation, qualitative analysis and quantitative analysis of small nucleolar RNA molecules used for distinguishing cell de-servitization state in human and animal tissues and cells, and also relates to an application method for changing cell de-servitization state by regulating small nucleolar RNA in human and animal tissues and cells.

BACKGROUND ART

Small nucleolar RNA (snoRNA) is a kind of medium-length non-coding small RNA with a length ranging from 60 to 300 nt, which can bind with nucleolar ribonucleoprotein to form snoRNP complex. In vertebrates, genes encoding small nucleolar RNA mainly exist in the intron region of protein-coding genes or non-protein-coding genes, and mature small nucleolar RNA is formed after further post-transcriptional processing. In human cells, post-transcriptional modification of RNA, mRNA stability and translation control are important components of gene expression regulation. SnoRNA and its functional short RNA play an important role in these processes: they guide the modification of ribosomal RNA (rRNA) and small nuclear RNA (snRNA), affect the splicing of their complementary precursor mRNA, and control the translation and stability of mRNA. External factors and signal cascade reactions in cells can lead to the change of snoRNA expression level, and then cause physiological changes at cell level, organ dysfunction and various diseases. Through the detection and regulation of snoRNA, we can effectively determine and change the servitization state and de-servitization state of cells.

Because the research on different servitization states of cells has just started, there is no effective molecular marker to define the servitization state and de-servitization state of cells.

Therefore, it is urgent to establish effective snoRNA detection and regulation methods in this field.

SUMMARY OF THE INVENTION

At present, in the medical clinical process, there are many physiological phenomena that cannot be explained, such as hepatitis patients can't be excessively tired, renal tumor patients will die because of renal failure although the tumor foci is very small, human vegetable has no normal reflex but their physiological state is normal, and so on. Through the study of cell de-servitization state, we can further help to better explain these problems. The premise of this series of studies is to find a marker that can identify this state.

The inventor selects small nucleolar ribonucleic acid as a research object, it is hoped that this phenomenon can be distinguished by detecting the expression changes of small nucleolar RNA in cells, and at the same time, it is hoped that the cells will be further changed from de-servitization state to servitization state by regulating the expression of small nucleolar RNA in cells, so as to play a therapeutic role in clinic.

It is an object of present invention to firstly provide a detection marker for cell de-servitization state, which comprises any one or more of the following detectable snoRNA present in animal and plant cells, preferably any two or more of the following snoRNA, and the sequence of snoRNA sees http://snoopy.med.miyazaki-u.ac.jp/.

It is another object of the present invention to provide a detection method of snoRNA marker for detecting the above cell de-servitization state, and the state of the cells can be further evaluated by above method.

It is another object of the present invention to provide a method for regulating snoRNA in an organism, the servitization state and the de-servitization state of a cell can be switched by regulating snoRNA.

In the first aspect of the present invention, it provides a use of small nucleolar RNA (snoRNA) or a detection reagent thereof for preparing a reagent or a kit for detecting a servitization state of a cell.

In another preferred embodiment, the servitization state comprises an enmunting state, a demunting state, or a transition thereof.

In another preferred embodiment, the snoRNA is derived from mammals, rodents and primates.

In another preferred embodiment, the snoRNA is derived from human and mouse.

In another preferred embodiment, the snoRNA is organ, tissue, cell-specific snoRNA.

In another preferred embodiment, the organs are selected from the group consisting of joint, ligament, tongue, salivary gland, parotid gland, mandibular gland, sublingual gland, pharynx, esophagus, stomach, small intestine, duodenum, jejunum, ileum, large intestine, liver, gallbladder, mesentery, pancreas, nasal cavity, pharynx, larynx, trachea, bronchus, lung, diaphragm, kidney, ureter, bladder, urethra, ovary, oviduct, uterus, vagina, placenta, testis, epididymis, deferens, seminal vesicle, prostate, bulbar urethral gland, penis, scrotum, pituitary, pineal, thyroid, parathyroid, adrenal gland, pancreas, heart, arteries, veins, microvessels, lymphatic vessels, lymph nodes, bone marrow, thymus, spleen, intestine-associated lymphoid tissue, tonsils, brain, diencephalon, brainstem, midbrain, pons, medulla oblongata, cerebellum, spinal cord, ventricles, choroid plexus, cranial nerves, spinal nerves, ganglia, enteric nervous system, cornea, iris, ciliary body, lens, retina, earlobe, tympanic membrane, ossicles, cochlea, ear vestibule, semicircular canal, tongue and skin, etc.

In another preferred embodiment, the tissue is selected from the group consisting of epithelial tissue (monolayer epithelial tissue, monolayer columnar epithelial tissue, pseudostratified ciliated epithelial tissue, stratified cubic epithelial tissue), connective tissue (adipose tissue, loose connective tissue, fibrous connective tissue, hyaline cartilage tissue, elastic cartilage tissue, fibrous cartilage tissue, bone tissue, blood tissue), nerve tissue and muscle tissue (myocardium, skeletal muscle, smooth muscle).

In another preferred embodiment, the cells include cells derived from the endoderm including exocrine epithelial cells, barrier cells, and hormone secreting cells. The exocrine epithelial cells include the Brunner's gland cell in duodenum, goblet cells in respiratory tract and digestive tract, pit cells, chief cells, parietal cells in stomach, pancreatic acinar cells, Paneth cell in small intestine, lung type II alveolar cells and rod cells in lung. Barrier cells include type I lung cells, gallbladder epithelial cells, centroacinar cells, intercalated duct cells and intestinal brush margin cells. There are four types of hormone secreting cells: intestinal endocrine cells, thyroid cells, parathyroid cells and islet cells. Intestinal endocrine cells include K cells, L cells, I cells, G cells, enterochromaffin cells, enterochromaffin-like cells, N cells, S cells, D cells and Mo cells. Thyroid cells include thyroid epithelial cells and parafollicular cells. Parathyroid cells include parathyroid main cells and eosinophils. Islet cells include Alpha cells, Beta cells, Delta cells, Epsilon cells and pp cells. Cells derived from ectoderm mainly include exocrine epithelial cells, hormone secreting cells, epithelial cells, nervous system cells and so on. Among them, exocrine cells include salivary gland mucus cells, salivary gland serous cells, Von Ebner's gland cell in tongue, mammary gland cells, lacrimal gland cells, earwax gland cells in ear, exocrine sweat gland dark cells, exocrine sweat gland bright cells, apocrine sweat gland cells, Gland of Moll cell in eyelid, adipose gland cells and Brunner's gland cell in duodenum. Hormone secreting cells include corticotropin cells, gonadotropin cells, prolactin cells, melanotropin cells, growth hormone cells and thyroid stimulating cells in the anterior and middle pituitary gland, large cell neurosecretory cells, small cell neurosecretory cells, chromaffin cells. Epithelial cells include keratinocytes, epidermal basal cells, melanocytes, medullary hair cells, cortical hair axons cells, epidermal hair axons cells, Huxley layer hair root sheath cells, outer root sheath hair cells, surface epithelial cells, basal cells, intercalated duct cells, striated tube cells, lactiferous duct cells and ameloblasts. Cells in the nervous system are divided into five categories: sensor cells, autonomic nerve cells, sensory organs and peripheral neuron supporting cells, central nervous system neurons and glial cells, lens cells. Sensor cells include cortical auditory inner hair cells, cortical auditory outer hair cells, basal cells of olfactory epithelium, cold sensitive primary sensory neurons, heat-sensitive primary sensory neurons, epidermal Merkel cells, olfactory receptor neurons, pain-sensitive primary sensory neurons, proprioceptive primary sensory neurons, tactile-sensitive primary sensory neurons, carotid somatic cytochemical receptor ball cells, outer hair cells of ear vestibular system, inner hair cells of ear vestibular system, taste receptor cells of taste buds, retinal photoreceptor cells, wherein retinal photoreceptor cells can be subdivided into photoreceptor rod cells, photoreceptor blue sensitive cone cells, photoreceptor green sensitive cone cells and photoreceptor red sensitive cone cells. Autonomic nerve cells include cholinergic nerve cells, adrenergic nerve cells and polypeptide nerve cells. Sertoli cells of sensory organs and peripheral neurons include intracortical column cells, extracortical column cells, intracortical finger cells, extracortical finger cells, cortical marginal cells, cortical Hensen cells, vestibular Sertoli cells, taste bud Sertoli cells, olfactory epithelial Sertoli cells, Schwann cells, satellite glial cells and intestinal glial cells. Neurons and glial cells in the central nervous system include neuronal cells, astrocytes, oligodendrocytes, ependymal cells, pituitary cells, wherein neurons cells can be divided into interneurons and principal cells, interneurons include basket cells, wheel cells, stellate cells, golgi cells, granulosa cells, Lugaro cells, unipolar brush cells, Martinotti cells, chandelier cells, Cajal-Retzius cells, Double-bouquet cells, glial cells, retinal horizontal cells, amacrine cells, spinal cord interneurons and Renshaw cells; principal cells include principal axis neurons, fork neurons, pyramidal cells, stellate cells, boundary cells, hairy cells, Purkinje cells and medium-sized spiny neurons, wherein pyramidal cells include position cells, location cells, velocity cells, direction identification cells and giant pyramidal cells. Lens cells include lens epithelial cells and lens fiber cells. The cells derived from mesoderm mainly include metabolic and storage cells, secretory cells, barrier cells, extracellular stromal cells, contractile cells, blood and immune system cells, germ cells, trophoblast cells and interstitial tissue cells. Metabolic and storage cells include white adipocytes, brown adipocytes and liver adipocytes. Secretory cells include three types of adrenal cortex cells including adrenal cortical zona globularis cells producing mineralocorticoids, adrenal cortical fascicular cells producing glucocorticoids and adrenal cortical reticular zone cells producing androgen, ovarian follicular intimal cells, granular lutein cells, luteal cells, testicular interstitial cells, seminal vesicle cells, prostate cells, bulbar gland cells, pasteurian gland cells, urethral or periurethral gland cells, endometrial cells, paraglomerular cells, renal dense plaque cells, renal peripolar cells, renal mesangial cells. Barrier cells can be divided into three types: podocytes, proximal tubule brush margin cells, Henry's ring thin segment cells, renal distal tubule cells, main cells and intercalary cells in renal collecting duct cells, and transitional epithelial cells in urinary system; ductal cells, efferent ductal cells, epididymal principal cells and epididymal basal cells in reproductive system; endothelial cells in the circulatory system. Extracellular stromal cells include ear vestibular semicircular canal epithelial cells, cortical interdentate epithelial cells, loose connective tissue fibroblasts, corneal fibroblasts, tendon fibroblasts, bone marrow reticular fibroblasts, other non-epithelial fibroblasts, pericytes, such as hepatic stellate cells, intervertebral disc nucleus pulposus cells, hyaline chondrocytes, fibrochondrocytes, elastic chondrocytes, osteoblasts, bone progenitor cells, vitreous clear cells, extraaural lymphatic space stellate cells, pancreatic stellate cells. Contractile cells include six types of skeletal muscle cells including red skeletal muscle cells, white skeletal muscle cells, intermediate skeletal muscle cells, muscular spindle nucleus bag cells, muscular spindle nucleus chain cells and muscular satellite cells, three kinds of cardiomyocytes including myocardial cells, sinoatrial node cells and Purkinje fiber cells, smooth muscle cells, iris myoepithelial cells and exocrine gland myoepithelial cells. Blood and immune system cells includes red blood cells, megakaryocytes, platelets, monocytes, macrophages in connective tissue, langerhans cells in the epidermis, osteoclasts, dendritic cells, microglia, neutrophils, eosinophils, basophils, hybridoma cells, mast cells, helper T cells, suppressor T cells, cytotoxic T cells, natural killer T cells, B cells, natural killer cells, reticular cells, stem cells and progenitor cells of blood and immune system. Germ cells include oogonia/oocytes, spermatocytes, spermatogonia, spermatocytes and sperm. Trophoblasts include granulosa cells in ovary, Sertoli cells in testis and epithelial reticular cells. Interstitial tissue cells include interstitial tissue kidney cells.

In another preferred embodiment, the snoRNA is one or more of the snoRNA shown in Table 1 or a combination thereof.

In another preferred embodiment, the snoRNA is selected from the group consisting of SNORA41, SNORD85, SNORD115, SNORD116, SNORD14c, SNORD14d, SNORD55, SNORD15b, SNORD23, SNORD96a, SNORD123, SNORD34, and SNORD82.

In the second aspect of the invention, it provides a method for determining a molecular marker of a servitization state, comprising the steps of:
(1) providing cells in the first servitization state, detecting the type and quantity of snoRNA in the first servitization state to obtain a first data set;
(2) providing cells in a second servitization state, detecting the type and quantity of snoRNA in the second servitization state to obtain a second data set;
(3) comparing the first data set with the second data set to determine the type and quantity information of snoRNA specific to the first servitization state and the second servitization state, thereby identifying the molecular markers specific to the first servitization state and the second servitization state.

In another preferred embodiment, the first servitization state is an enmunting state.

In another preferred embodiment, the second servitization state is a demunting state.

In another preferred embodiment, the snoRNA is derived from mammals, rodents and primates.

In another preferred embodiment, the snoRNA is derived from human and mouse.

In another preferred embodiment, the snoRNA is organ, tissue, cell-specific snoRNA.

In another preferred embodiment, the organs include joint, ligament, tongue, salivary gland, parotid gland, mandibular gland, sublingual gland, pharynx, esophagus, stomach, small intestine, duodenum, jejunum, ileum, large intestine, liver, gallbladder, mesentery, pancreas, nasal cavity, pharynx, larynx, trachea, bronchus, lung, diaphragm, kidney, ureter, bladder, urethra, ovary, oviduct, uterus, vagina, placenta, testis, epididymis, deferens, seminal vesicle, prostate, bulbar urethral gland, penis, scrotum, pituitary, pineal, thyroid, parathyroid, adrenal gland, pancreas, heart, arteries, veins, microvessels, lymphatic vessels, lymph nodes, bone marrow, thymus, spleen, intestine-associated lymphoid tissue, tonsils, brain, diencephalon, brainstem, midbrain, pons, medulla oblongata, cerebellum, spinal cord, ventricles, choroid plexus, cranial nerves, spinal nerves, ganglia, enteric nervous system, cornea, iris, ciliary body, lens, retina, earlobe, tympanic membrane, ossicles, cochlea, ear vestibule, semicircular canal, tongue and skin, etc.

In another preferred embodiment, the tissue comprises epithelial tissue (monolayer epithelial tissue, monolayer columnar epithelial tissue, pseudostratified ciliated epithelial tissue, stratified cubic epithelial tissue), connective tissue (adipose tissue, loose connective tissue, fibrous connective tissue, hyaline cartilage tissue, elastic cartilage tissue, fibrous cartilage tissue, bone tissue, blood tissue), nerve tissue and muscle tissue (myocardium, skeletal muscle, smooth muscle).

In another preferred embodiment, the cells include cells derived from the endoderm including exocrine epithelial cells, barrier cells, and hormone secreting cells. The exocrine epithelial cells include the Brunner's gland cell in duodenum, goblet cells in respiratory tract and digestive tract, pit cells, chief cells, parietal cells in stomach, pancreatic acinar cells, Paneth cell in small intestine, lung type II alveolar cells and rod cells in lung. Barrier cells include type I lung cells, gallbladder epithelial cells, centroacinar cells, intercalated duct cells and intestinal brush margin cells. There are four types of hormone secreting cells: intestinal endocrine cells, thyroid cells, parathyroid cells and islet cells. Intestinal endocrine cells include K cells, L cells, I cells, G cells, enterochromaffin cells, enterochromaffin-like cells, N cells, S cells, D cells and Mo cells. Thyroid cells include thyroid epithelial cells and parafollicular cells. Parathyroid cells include parathyroid main cells and eosinophils. Islet cells include Alpha cells, Beta cells, Delta cells, Epsilon cells and pp cells. Cells derived from ectoderm mainly include exocrine epithelial cells, hormone secreting cells, epithelial cells, nervous system cells and so on. Among them, exocrine cells include salivary gland mucus cells, salivary gland serous cells, Von Ebner's gland cell in tongue, mammary gland cells, lacrimal gland cells, earwax gland cells in ear, exocrine sweat gland dark cells, exocrine sweat gland bright cells, apocrine sweat gland cells, Gland of Moll cell in eyelid, adipose gland cells and Brunner's gland cell in duodenum. Hormone secreting cells include corticotropin cells, gonadotropin cells, prolactin cells, melanotropin cells, growth hormone cells and thyroid stimulating cells in the anterior and middle pituitary gland, large cell neurosecretory cells, small cell neurosecretory cells, chromaffin cells. Epithelial cells include keratinocytes, epidermal basal cells, melanocytes, medullary hair cells, cortical hair axons cells, epidermal hair axons cells, Huxley layer hair root sheath cells, outer root sheath hair cells, surface epithelial cells, basal cells, intercalated duct cells, striated tube cells, lactiferous duct cells and ameloblasts. Cells in the nervous system are divided into five categories: sensor cells, autonomic nerve cells, sensory organs and peripheral neuron supporting cells, central nervous system neurons and glial cells, lens cells. Sensor cells include cortical auditory inner hair cells, cortical auditory outer hair cells, basal cells of olfactory epithelium, cold sensitive primary sensory neurons, heat-sensitive primary sensory neurons, epidermal Merkel cells, olfactory receptor neurons, pain-sensitive primary sensory neurons, proprioceptive primary sensory neurons, tactile-sensitive primary sensory neurons, carotid somatic cytochemical receptor ball cells, outer hair cells of ear vestibular system, inner hair cells of ear vestibular system, taste receptor cells of taste buds, retinal photoreceptor cells, wherein retinal photoreceptor cells can be subdivided into photoreceptor rod cells, photoreceptor blue sensitive cone cells, photoreceptor green sensitive cone cells and photoreceptor red sensitive cone cells. Autonomic nerve cells include cholinergic nerve cells, adrenergic nerve cells and polypeptide nerve cells. Sertoli cells of sensory organs and peripheral neurons include intracortical column cells, extracortical column cells, intracortical finger cells, extracortical finger cells, cortical marginal cells, cortical Hensen cells, vestibular Sertoli cells, taste bud Sertoli cells, olfactory epithelial Sertoli cells, Schwann cells, satellite glial cells and intestinal glial cells. Neurons and glial cells in the central nervous system include neuronal cells, astrocytes, oligodendrocytes, ependymal cells, pituitary cells, wherein neurons cells can be divided into interneurons and principal cells, interneurons include basket cells, wheel cells, stellate cells, golgi cells, granulosa cells, Lugaro cells, unipolar brush cells, Martinotti cells, chandelier cells, Cajal-Retzius cells, Double-bouquet cells, glial cells, retinal horizontal cells, amacrine cells, spinal cord interneurons and Renshaw cells; principal cells include principal axis neurons, fork neurons, pyramidal cells, stellate cells, boundary cells, hairy cells, Purkinje cells and medium-sized spiny neurons, wherein pyramidal cells include position cells, location cells, velocity cells, direction identification cells and giant pyramidal cells. Lens cells include lens epithelial cells and lens fiber cells. The cells derived from mesoderm mainly include metabolic and storage cells, secretory cells, barrier cells, extracellular stromal cells, contractile cells, blood and immune system cells, germ cells, trophoblast cells and interstitial tissue cells. Metabolic and storage cells include white adipocytes, brown adipocytes and liver adipocytes. Secretory cells include three types of adrenal cortex cells including adrenal cortical zona globularis cells producing mineralocorticoids, adrenal cortical fascicular cells producing glucocorticoids and adrenal cortical reticular zone cells producing androgen, ovarian follicular intimal cells, granular lutein cells, luteal cells, testicular interstitial cells, seminal vesicle cells, prostate cells, bulbar gland cells, pasteurian gland cells, urethral or periurethral gland cells, endometrial cells, paraglomerular cells, renal dense plaque cells, renal peripolar cells, renal mesangial cells. Barrier cells can be divided into three types: podocytes, proximal tubule brush margin cells, Henry's ring thin segment cells, renal distal tubule cells, main cells and intercalary cells in renal collecting duct cells, and transitional epithelial cells in urinary system; ductal cells, efferent ductal cells, epididymal principal cells and epididymal basal cells in reproductive system; endothelial cells in the circulatory system. Extracellular stromal cells include ear vestibular semicircular canal epithelial cells, cortical interdentate epithelial cells, loose connective tissue fibroblasts, corneal fibroblasts, tendon fibroblasts, bone marrow reticular fibroblasts, other non-epithelial fibroblasts, pericytes, such as hepatic stellate cells, intervertebral disc nucleus pulposus cells, hyaline chondrocytes, fibrochondrocytes, elastic chondrocytes, osteoblasts, bone progenitor cells, vitreous clear cells, extraaural lymphatic space stellate cells, pancreatic stellate cells. Contractile cells include six types of skeletal muscle cells including red skeletal muscle cells, white skeletal muscle cells, intermediate skeletal muscle cells, muscular spindle nucleus bag cells, muscular spindle nucleus chain cells and muscular satellite cells, three kinds of cardiomyocytes including myocardial cells, sinoatrial node cells and Purkinje fiber cells, smooth muscle cells, iris myoepithelial cells and exocrine gland myoepithelial cells. Blood and immune system cells includes red blood cells, megakaryocytes, platelets, monocytes, macrophages in connective tissue, langerhans cells in the epidermis, osteoclasts, dendritic cells, microglia, neutrophils, eosinophils, basophils, hybridoma cells, mast cells, helper T cells, suppressor T cells, cytotoxic T cells, natural killer T cells, B cells, natural killer cells, reticular cells, stem cells and progenitor cells of blood and immune system. Germ cells include oogonia/oocytes, spermatocytes, spermatogonia, spermatocytes and sperm. Trophoblasts include granulosa cells in ovary, Sertoli cells in testis and epithelial reticular cells. Interstitial tissue cells include interstitial tissue kidney cells, etc.

In another preferred embodiment, the snoRNA is selected from the group consisting of SNORA41, SNORD85, SNORD115, SNORD116, SNORD14c, SNORD14d, SNORD55, SNORD15b, SNORD23, SNORD96a, SNORD123, SNORD34, and SNORD82.

In another preferred embodiment, the method is non-diagnostic and non-therapeutic.

In the third aspect of the invention, it provides a use of snoRNA or a promoter or a antagonist thereof for the preparation of a medicament or preparation for regulating the servitization state of a cell, tissue or organ.

In another preferred embodiment, the servitization state comprises an enmunting state, a demunting state, or a transition thereof.

In another preferred embodiment, the snoRNA is one or more of the snoRNA shown in Table 1 or a combination thereof.

In another preferred embodiment, the snoRNA is selected from the group consisting of SNORA41, SNORD85, SNORD115, SNORD116, SNORD14c, SNORD14d, SNORD55, SNORD15b, SNORD23, SNORD96a, SNORD123, SNORD34, and SNORD82.

It should be understood that in the present invention, any of the technical features specifically described above and below (such as in the Examples) can be combined with each other to form a new or preferred technical solution, which will not redundantly be described one by one herein.

DETAILED DESCRIPTION OF THE INVENTION

Figure 1:
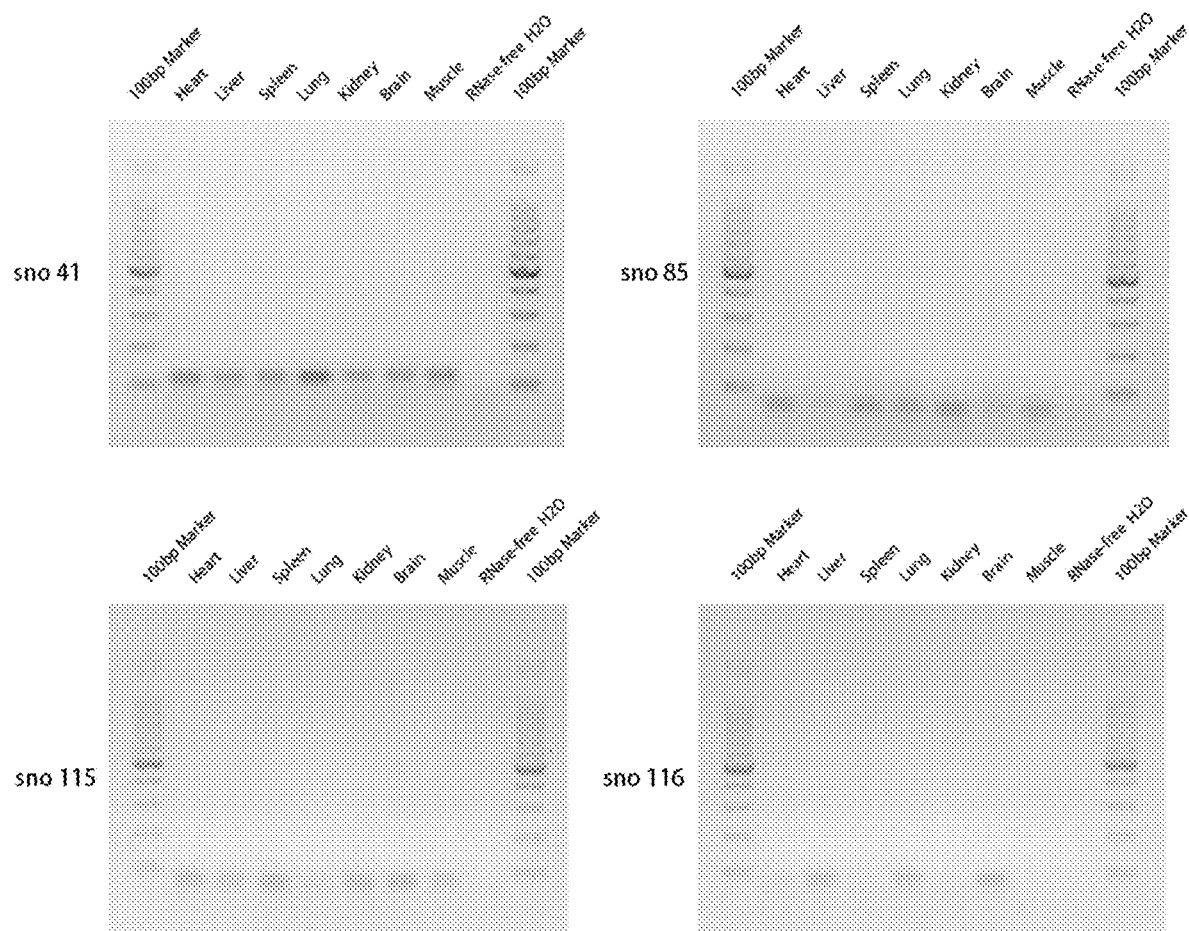
FIG. 1 shows the RT-PCR results of some snoRNA detected in various tissues of normal mice.

After extensive and in-depth research, the inventor discovered for the first time that by studying the specific changes of snoRNA in various tissues and cells under the servitization state and the de-servitization state, a class of snoRNA with large differential expression degree in the two states of cells can be obtained, which can be applied to a class of molecular markers for diagnosing cell states. At the same time, we study the changes of cell state after regulating snoRNA expression, and provide a method for switching between cell servitization state and de-servitization state for biological experiments and clinical applications. On above basis, the present invention has been completed.

Cell Servitization State

In-servitization: enmute (verb); enmunting (gerund); enmuntion (noun); enmuntive (adjective); enmunally (adverb)

De-servitization: demute (verb); demunting (gerund); demuntion (noun); demuntive (adjective); demuntly (adverb)

In the concept of classical cell biology, all mature cells with specific functions are called differentiated cells. If differentiated cells lack specific functions to regulate homeostasis or internal environment, they are simply called as "dedifferentiation", which is neither different from truly undifferentiated cells such as precursor cells nor distinguished by specific molecular markers.

The invention discovers that the differentiated cells have two states: one is In-servitization state (enmunting, which has the service function of regulating homeostasis), and the other is de-servitization state (demunting, which has no service function of regulating homeostasis). These two states are all differentiated, so the survival metabolism (related gene expression and protein synthesis) of cells is the same, and the service function is different. The difference between demunting cells and precursor cells is that they have different living and metabolic states (precursor cells have not yet been differentiated), but the state of specific service function loss is the same.

The elevation of tissue-specific SnoRNA is a biomarker for identifying demunting cells. Increasing SnoRNA can change the enmunting state into demunting state; reducing SnoRNA can change the demunting state of cells into enmunting state. All tissues and cells have these two states at the same time. Under most pathological conditions, the proportion of demunting cells will increase, which will lead to organ failure. Reducing the pathologically increased demunting cells will have therapeutic effects on all histopathological functional failures, such as awakening of brain-dead patients, functional nerve growth of paraplegic patients, and increasing the proportion of activated functional neurons in the brain.

The Main Advantages of the Invention Include:
1) The invention discovers two states of differentiated cells (enmunting state and demunting state), distinguishes demunting state cells from undifferentiated cells, and can explain many unexplained phenomena in original biological and medical research by studying these two states;
2) By establishing an effective snoRNA detection method, the invention can quickly and simply identify the enmunting state and the demunting state of cells, avoiding the need to identify the two cell states through complex research on cell function, state, transcriptome and proteome changes;
3) By establishing an effective snoRNA regulation method, the invention can effectively switch the enmunting state and the demunting state of cells, and has great application prospects in biological research and clinical application;
4) The invention further discovers the important regulation function of snoRNA in an organism, and provides a new direction for biological theoretical research and applied research.

The present invention will be further illustrated below with reference to the specific examples. It should be understood that these examples are only to illustrate the invention but not to limit the scope of the invention. In the following examples, the experimental methods without specific conditions are usually in accordance with conventional conditions, such as Sambrook et al., Molecular Cloning: Laboratory Manual (New York: Cold Spring Harbor Laboratory Press, 1989), or in accordance with the conditions recommended by the manufacturer. Unless otherwise stated, percentages and parts are percentages by weight and parts by weight.

General Method

The detection method of snoRNA marker for detecting cell demunting state is selected from reverse transcription polymerase chain reaction (RT-PCR), real-time fluorescence quantitative reverse transcription polymerase chain reaction (Real-time RT-PCR), Northern blotting, high-throughput sequencing technology or biochip method.

The RT-PCR method is the preferred method, comprising the following steps:
1) Extracting the total RNA of the tested cell sample (for example, using Trizol reagent), and obtaining a cDNA sample by RNA reverse transcription reaction; or using the lysate of the tested cell sample as buffer to carry out reverse transcription reaction to prepare cDNA samples;
2) Using snoRNA to design primers for PCR reaction;
3) Performing agarose gel electrophoresis of PCR products;
4) After EB staining, the results were observed under ultraviolet lamp.

The Real-time PCR method is another preferred method, comprising the following steps:
1) Extracting the total RNA of the tested cell sample (for example, using Trizol reagent), and obtaining a cDNA sample by RNA reverse transcription reaction; or using the lysate of the tested cell sample as buffer to carry out reverse transcription reaction to prepare cDNA samples;
2) Primers and fluorescent dye were designed with snoRNA for PCR reaction (see table for PCR primers of snoRNA);
3) Changes in the amount of snoRNA in the test cell sample relative to the normal cell sample were detected and compared.

The Northern blotting method comprises the following steps:
1) Extracting the total RNA of the tested cell sample (e.g. using Trizol reagent);
2) Conducting deformed PAGE electrophoresis and membrane transfer experiments;
3) Preparing isotope labeled or digoxin labeled nucleic acid probes;
4) Performing membrane hybridization reaction;
5) Detecting isotope signal or digoxin signal.

The high-throughput sequencing method comprises the following steps:
1) Extracting the total RNA of the tested cell sample (e.g. using Trizol reagent);
2) Conducting deformed PAGE electrophoresis to recover RNA molecules below 50 nt;
3) Linking the adapter primer enzyme to the 3' end and the 5' end of the RNA molecule;
4) Performing RT-PCR reaction and sequencing;
5) Data analysis and processing.

The biochip method comprises the following steps:
1) Lattice all more than 700 kinds of snoRNA libraries in people and prepare biochips;
2) Extracting the total RNA of the tested cell sample (e.g. using Trizol reagent);
3) Separating small ribonucleic acid by column separation;
4) Using T4RNA ligase to carry out micro-RNA fluorescence labeling;
5) Carrying out hybridization reaction with biochip.

The regulatory methods were selected from interfering RNA regulation and CRISPR/Cas9 regulation.

The interfering RNA regulation method is the preferred method and comprises the following steps:
1) Designing interfering RNA (siRNA sequence) and shRNA sequence capable of expressing interfering RNA (see excel for siRNA sequence and shRNA sequence);
2) Preparing the interfering RNA or plasmid/virus of shRNA capable of expressing corresponding interfering RNA;
3) Transferring interfering RNA or plasmid expressing interfering RNA into cells by transfection method or infecting cells by virus infection method;
4) Collecting cells to detect cell state.

CRISPR/Cas9 regulation is another preferred method comprising the following steps:
1) Designing sgRNA;
2) Constructing the sgRNA plasmid vector and simultaneously constructing aav virus expressing sgRNA and Cas9 protein;
3) Transfecting sgRNA plasmid and Cas9 plasmid into the target cell using a transfection method; or incubating the constructed aav virus with cells;
4) Collecting cells to detect cell state.

Example 1

RT-PCR Experiment of snoRNA in Cells

In order to detect the specific changes of snoRNA in different cell servitization states, RT-PCR technology was used to detect snoRNA content in human and animal cells. The specific steps were as follows:
(1) Collecting cells from humans or other animals;
(2) Preparing cDNA samples. The total RNA of cells was extracted by TRIzol reagent, and then cDNA was obtained by RNA reverse transcription reaction. The reaction system of reverse transcription included 2 μl 5×AMV buffer, 1 μl dNTP mixture, 0.5 μl RNAase Inhibitor, 0.5 μl AMV enzyme, 1 μl gene-specific reverse primer, 1 μg total RNA and supplemented RNAase free water to a total volume of 10 μl. The reaction steps were incubation at 16° C. for 15 minutes, reaction at 42° C. for 1 hour and incubation at 85° C. for 5 minutes.
(3) PCR electrophoresis and observation. 1 μl cDNA was taken from the previous reaction, 0.3 μl Taq enzyme, 0.4 μl dNTP mixture, 1.2 μl 25 mM MgCl2, 2 μl 10×PCR Buffer, 0.5 μl specific forward primer, 0.5 μl specific reverse primer and 14.1 μl water were added, and 20 μl system for PCR. The reaction conditions of PCR were as follows: 95° C., 5 minutes for one cycle→95° C., 15 seconds, 60 degrees Celsius, 1 minute for 40 cycles. 10 μl of PCR products were taken for 3% agarose gel electrophoresis, and then observed under ultraviolet lamp after EB staining.

Results were shown in FIG. 1, the results of RT-PCR were obtained by extracting total RNA from multiple tissues of normal mice. The inventor selected more than 900 snoRNAs from mice for PCR reaction, and FIG. 1 showed four snoRNAs (SNORA41, SNORD85, SNORD115 and SNORD116). The results showed that these four snoRNAs can be detected in heart, liver, spleen, lung, kidney, brain and muscle.

Example 2

Real-Time PCR Assay of snoRNA in Cells

In order to detect the specific changes of snoRNA in different cell servitization states, real-time PCR was used to detect the snoRNA content in human and animal cells. The experimental principle and procedure of Real-time PCR were the same as RT-PCR, the only difference was that the fluorescent dye Eva Green was added in PCR. The instrument used was ABI Prism 7300 fluorescence quantitative PCR instrument, and the reaction conditions were 95° C., 5 minutes for one cycle→95° C., 15 seconds, 60 degrees Celsius, 1 minute for 40 cycles. The data processing method was ΔΔ CT method, and CT was set as the number of cycles when the reaction reached the threshold, then the expression amount of each snoRNA relative to the standard internal reference can be expressed by equation $2^{-\Delta\ CT}$, where $\Delta CT = CT_{Sample} - CT_{Internal\ reference}$.

Figure 2:
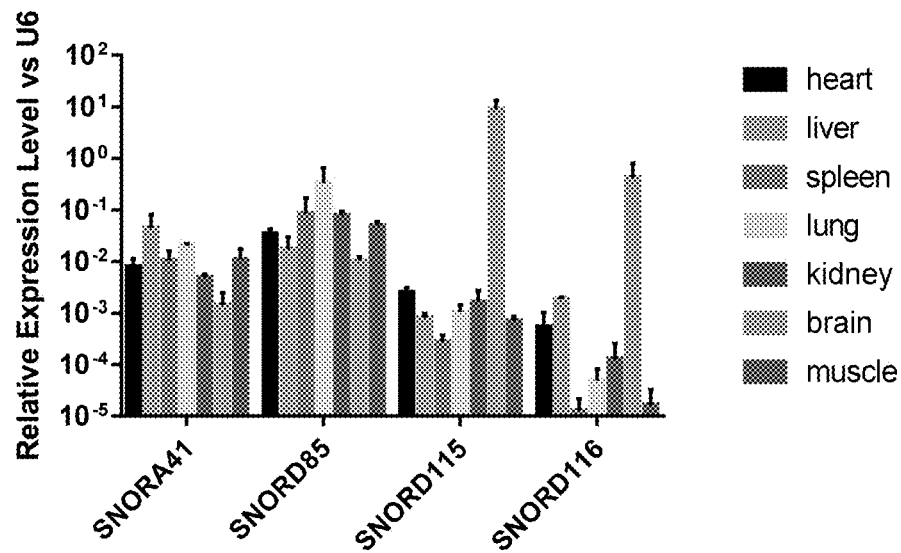
FIG. 2 shows the real-time PCR results of some snoRNA detected in various tissues of normal mice.

The result was shown in FIG. 2. The inventors used Real-time PCR to detect the expression of all snoRNA of mouse in various tissues. FIG. 2 showed only the expression levels of SNORA41, SNORD85, SNORD115 and SNORD116 in heart, liver, spleen, lung, kidney, brain and muscle, respectively. U6 was used as internal reference in the experiment. It can be known from the test results that SNORA41 is highly expressed in the liver, SNORD85 is highly expressed in the lung, spleen, muscle and kidney, and SNORD115 and SNORD116 are specifically highly expressed in brain tissue. From FIG. 2, it could be seen that there were tissue-specific expressed snoRNA in various tissues, and the differential expression of these snoRNA may be related to the different functions performed by different tissues in the body.

Example 3

Detection of snoRNA Content in Adipose Tissue In Vitro after Different Culture Time by High-Throughput Sequencing In order to detect whether snoRNA is differentially expressed in different cell states. The present inventors used a high-throughput sequencing method to detect snoRNA expression profiles of adipocytes at different time points after in vitro culture. The specific experimental steps were as follows:
(1) Collecting white adipose tissue of mice in different states. After cutting into small pieces, the adipocytes were collected at 0, 3, 6, 9, 12 and 24 hours respectively to extract total RNA and total protein.
(2) Isolating small RNA and establishing library. 18-30 nt RNA was separated from total RNA by PAGE electrophoresis gel cutting. 5-adenylated, 3-blocked single-stranded DNA linkers were used to link to the 3' end of RNA. Digestive enzymes were added and the 3' linker was removed. The 5' linker was linked to the 5' end of the product in the previous step. RT primers were used for reverse transcription extension to synthesize one strand cDNA. High-sensitivity polymerase was used to amplify cDNA, and the cDNA linked with 3' and 5' linkers was enriched to enlarge the library yield. PCR products in the range of 100-120 bp were separated by PAGE electrophoresis, and by-products such as primer dimer were effectively removed. The quality of the constructed library was tested, and the qualified library was sequenced on computer.
(3) The cDNA library was sequenced using Illumina Hiseq 2500.
(4) Sequencing data generation and subsequent analysis. After the sequencing image files were converted into sequence files using CASAVA, the tags with low sequencing quality, tags with 5' linker contamination, tags without 3' linker sequence, tags without inserts, tags containing polyA and tags less than 18 nt were removed respectively. The remaining sequences were compared and annotated with known snoRNA using bowtie. The snoRNA expression profile of adipocytes in different states was obtained by summarizing all sample data.
(5) Real-time PCR and Western blotting were used to detect leptin mRNA and protein content in adipocytes at each time point in step (1).

Figure 3:
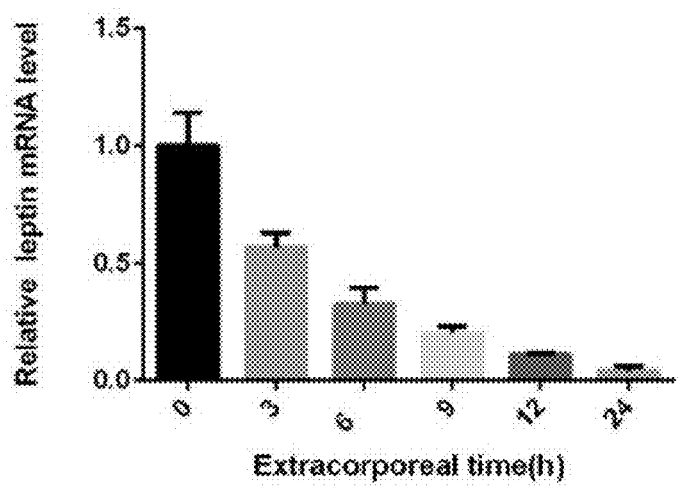
FIG. 3 shows the changes of leptin gene expression at different time points after adipocyte culture in vitro.
Figure 3:
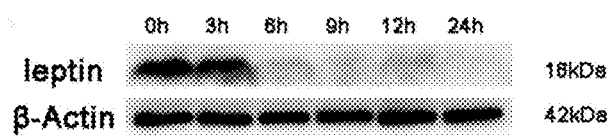

Results were as shown in FIG. 3, the present inventor detected the expression levels of service genes specific to adipocytes, such as leptin, in adipocytes at different time points. FIG. 2 only showed the change of leptin gene expression content. The results showed that both mRNA level and protein level of leptin gene decreased with the increase of culture time in vitro until it was no longer expressed. It showed that adipocytes changed from enmunting state to demunting state after being taken in vitro.

Figure 4:
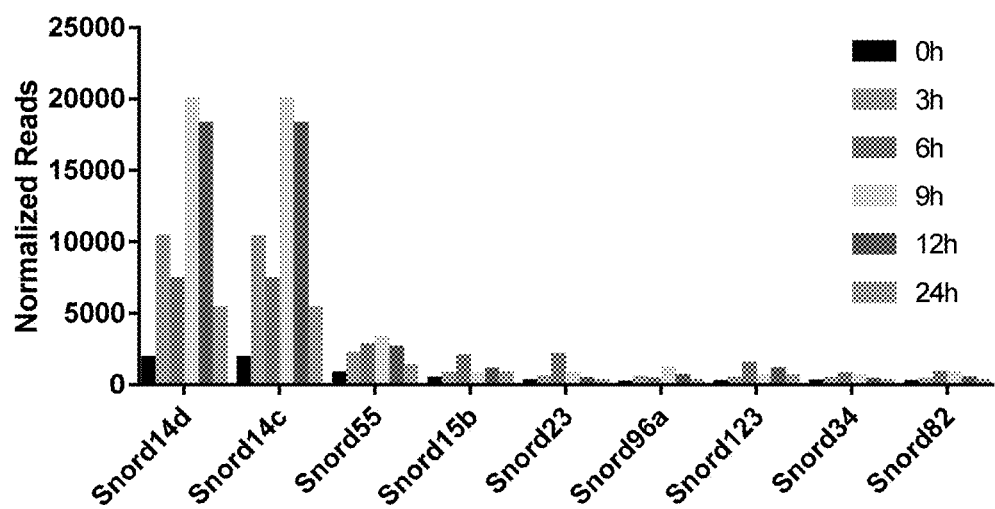
FIG. 4 shows the expression profile of snoRNA in adipocytes in different states detected by high-throughput sequencing.

As shown in FIG. 4, by analyzing the expression profiles of snoRNA in adipose tissue at different time points, the inventors found that the expression levels of snoRNA such as SNORD14c/d, SNORD55, SNORD15b, SNORD23, SNORD96a, SNORD123, SNORD34 and SNORD82 changed with time. These nine snoRNA began to increase after 3 h in vitro culture, reached the highest level at 9 h, and then decreased after 24 h. The above data showed that after being cultured in vitro, adipocytes gradually turned into a de-servitization state with the change of external conditions, the expression of snoRNA also increased. These results suggested that these snoRNA can be used as molecular markers of adipocyte de-servitization state.

TABLE 1

Artificial sequence or cDNA sequence corresponding to SnoRNA

| SnoRNA | Sequence | SEQ ID No.: |
|---|---|---|
| Snord14d | TCGCTGTGATGATGGATTCCAAAACCATTCGTA GTTTCCACCAGAAATGCTGTGTTGGCTAGTTCCT TCCTTGGATGTCTGAGCGAA | 1 |
| Snord14c | TCGCTGTGATGATGGATTCCAAAACCATTCGTA GTTTCCACCAGAAGTACTGTGTTGGCTAGTTCCT TCCTTGGATGTCTGAGCGAA | 2 |
| Snord55 | CGCGGATGATGACACCTGGGTATGCTGCACACT CCCGACTGCGTCGTGGGGAAGCCAACCTTGGAG AGCTGAGCGTGC | 3 |
| Snord15b | CTTCAGTGATGACACGATGACGAGTCAGAATGG CCACGTCTTGCTCTTGGTCCCTGTCAGTGCCATG TTCTGTGGTGCTGTACATGGTTCCCTTGGCAAAA GTGTCCTGCGCACTGATTGATTTAGAGGCATTTG TCTGAGAAGG | 4 |
| Snord23 | TGATAACCATCCTTGCTCCCCGTGCCTACTCGGG CTGTGGGCGACACCATGGCTGCCCTGGGCTGGG CCAGTTGGGCCATTGCCTGGGGACTGAGGGCA | 5 |
| Snord96a | ATCCTAGTGATGACAAGACGACATTGTCAACCA ATCCCCCACAAGGGAATGAGGACATGTCCTGCA ATTCTGAATGG | 6 |
| Snord123 | AAACCCATTGGTGAAAATGATGAATTCTGGGGC GCTGATTCATGTGACTTGAAAAAACGCCATCCA TTTCCTGACTCACCGCAGATTC | 7 |

TABLE 1-continued

Artificial sequence or cDNA sequence corresponding to SnoRNA

| SnoRNA | Sequence | SEQ ID No.: |
|---|---|---|
| Snord34 | CGTCTGTGATGTTCTGCTATTACCTACATTGTTT GAGCCTCATGAAAACCCCACTGGCTGAGACGC | 8 |
| Snord82 | ACAAGTGATGAGTGACAAAGGGACTTAATACT GAACCATGGGGTTGAAATGAAATATGCTGATGT GCT | 9 |

Example 4

Using siRNA Expressed by Plasmid to Inhibit the Expression of SNORD115 in Mouse Brain The inventor used restriction endonuclease to treat the control plasmid, after the linear vector was recovered, and T4 ligase was used to connect the RVG-SNORD115 shRNA combination fragment with the vector; the obtained ligation product was transformed and coated on the resistant plate; the next day, monoclones were selected and sequenced to determine the correctness of plasmid sequence.

The control plasmid and SNORD115 siRNA/RVG plasmid were injected into the tail vein of normal mice at a dose of 10 mg/kg; after 12 hours, the mice were killed, and the liver tissue and brain tissue of mice were taken for in situ hybridization experiment. In this experiment, green fluorescence modification was added to the sequence that was complementarily paired with the SNORD115 siRNA sequence as a detection probe to indicate the distribution of siRNA in tissue slices; the results showed that a large amount of siRNA was distributed in the liver tissue of mice, and a small amount of siRNA could be detected in the brain tissue of mice, which proved that SNORD115 siRNA/RVG plasmid really had brain targeting effect.

In order to prove whether these distributed siRNA can effectively inhibit the expression of SNORD115 in vivo, the inventors also injected the control plasmid and the SNORD115 siRNA/RVG plasmid at a dose of 10 mg/kg into the tail vein of mice, once every two days for a total of 7 times, killed the mice 24 hours after the last injection, and the brain tissue of the mice was taken for Real-time PCR experiment. The results showed that the expression level of SNORD115 in brain tissue could be effectively decreased by plasmid in vivo.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for detecting a servitization state of a cell by using a small nucleolar RNA (snoRNA), the use comprising:
   a) extracting a total RNA from the cell;
   b) determining if the snoRNA is present in the total RNA; and
   c) designating the cell to demunting state if the snoRNA is present in the total RNA, and designating the cell to enmunting state if the snoRNA sequence is not present in the total RNA;
   d) when the cell is at demunting state, the cell will be further changed from demunting state to enmunting state by regulating the expression of snoRNA in the cell, so as to play a therapeutic role in clinic;
   the snoRNA is from an organ, a tissue or a cell specific snoRNA;
   the organ is selected from the group consisting of liver, brain, diencephalon, brainstem, midbrain, pons, cerebellum, ventricles, and cranial nerves;
   the cell is selected from the group consisting of: hormone secreting cell, metabolic and storage cell;
   the hormone secreting cell is selected from the group consisting of intestinal endocrine cells, thyroid cells, parathyroid cells and islet cells;
   the metabolic and storage cell is selected from the group consisting of white adipocytes, brown adipocytes and liver adipocytes;
   the snoRNA is selected from the group consisting of SNORD115, SNORD116, SNORD14c, SNORD14d, SNORD55, SNORD15b, SNORD23, SNORD96a, SNORD123, SNORD34, and SNORD82.

2. The method according to claim 1, wherein the snoRNA is derived from a mammal, a rodent, or a primate.

3. The method according to claim 1, wherein the organ is selected from the group consisting of liver, and brain.

4. The method according to claim 1, wherein the tissue is selected from the group consisting of epithelial tissue, connective tissue, nerve tissue, and adipose tissue.

5. The method of claim 1, wherein the snoRNA is selected from the group consisting of SNORD14c, SNORD14d, SNORD55.

6. The method according to claim 1, wherein the snoRNA is selected from the group consisting of SNORD115, SNORD116, SNORD14c, SNORD14d, SNORD55 and SNORD15b.

* * * * *